United States Patent
Eigentler et al.

(10) Patent No.: US 11,660,447 B2
(45) Date of Patent: May 30, 2023

(54) MRI-SAFE AND FORCE-OPTIMIZED IMPLANTABLE RING MAGNET SYSTEM WITH AN ENHANCED INDUCTIVE LINK

(71) Applicant: MED-EL Elektromedizinische Geraete GmbH, Innsbruck (AT)

(72) Inventors: Thomas Wilhelm Eigentler, Sistrans (AT); Andreas Hofner, Innsbruck (AT); Ingeborg Hochmair, Axams (AT)

(73) Assignee: MED-EL Elektromedizinische Geraete GmbH, Innsbruck (AT)

( * ) Notice: Subject to any disclaimer, the term of this patent is extended or adjusted under 35 U.S.C. 154(b) by 0 days.

(21) Appl. No.: 17/684,023

(22) Filed: Mar. 1, 2022

(65) Prior Publication Data

US 2022/0176111 A1 Jun. 9, 2022

Related U.S. Application Data (63) Continuation of application No. 16/634,247, filed as application No. PCT/US2018/043589 on Jul. 25, 2018, now abandoned.

(Continued)

(51) Int. Cl.
*A61N 1/375* (2006.01)
*A61N 1/08* (2006.01)
(Continued)

(52) U.S. Cl.
CPC .......... *A61N 1/086* (2017.08); *A61N 1/36038* (2017.08); *A61N 1/375* (2013.01); *A61N 1/37229* (2013.01)

(58) Field of Classification Search
CPC ............ A61N 1/36038; A61N 1/36036; A61N 1/37229; A61N 1/375; A61N 1/37578
See application file for complete search history.

(56) References Cited

U.S. PATENT DOCUMENTS

| 4,352,960 A | 10/1982 | Dormer et al. |
| RE32,497 E | 9/1987 | Canfield |

(Continued)

FOREIGN PATENT DOCUMENTS

WO   WO 2017/027045 A1   2/2017

OTHER PUBLICATIONS

International Searching Authority/US, International Search Report and Written Opinion of the International Searching Authority, Application No. PCT/US2018/043589, dated Oct. 2, 2018, 14 pages.

(Continued)

*Primary Examiner* — George R Evanisko
(74) *Attorney, Agent, or Firm* — Sunstein LLP (57) ABSTRACT

A magnetic system for a medical implant system is described. A planar implant receiver coil is configured to lie underneath and parallel to overlying skin of an implanted patient for transcutaneous communication of an implant communications signal. A planar ring-shaped attachment magnet also is configured to lie underneath and parallel to the overlying skin and radially surrounds the receiver coil. The attachment magnet is characterized by a magnetic field configured to avoid creating torque on the attachment magnet in the presence of an external magnetic field.

11 Claims, 7 Drawing Sheets

Related U.S. Application Data (60) Provisional application No. 62/540,117, filed on Aug. 2, 2017.

(51) Int. Cl.
*A61N 1/36* (2006.01)
*A61N 1/372* (2006.01)

(56) References Cited

U.S. PATENT DOCUMENTS

| | | |
|---|---|---|
| RE32,947 E * | 6/1989 | Dormer .............. A61N 1/37223 |
| | | 607/57 |
| 5,314,453 A | 5/1994 | Jeutter |
| 6,178,353 B1 | 1/2001 | Griffith et al. |
| 6,838,963 B2 | 1/2005 | Zimmerling et al. |
| 8,024,047 B2 | 9/2011 | Olson et al. |
| 2011/0022120 A1 | 1/2011 | Ball et al. |
| 2012/0146576 A1 | 6/2012 | Partovi |
| 2014/0012071 A1 | 1/2014 | Nagl et al. |

OTHER PUBLICATIONS

European Patent Office, Extended European Search Report, Application No. 18842339.6, dated Apr. 23, 2020, 7 pages.

* cited by examiner

MRI-SAFE AND FORCE-OPTIMIZED IMPLANTABLE RING MAGNET SYSTEM WITH AN ENHANCED INDUCTIVE LINK

This application is a continuation of U.S. application Ser. No. 16/634,247, filed Jan. 27, 2020, which in turn is a 371 national phase entry of Patent Cooperation Treaty Application PCT/US2018/043589, filed Jul. 25, 2018, which in turn claims priority from U.S. Provisional application 62/540,117, filed Aug. 2, 2017, each of which are hereby incorporated herein by reference in its entirety.

FIELD OF THE INVENTION

The present invention relates to medical implants, and more specifically to a permanent magnet arrangement for use in such implants.

BACKGROUND ART

Figure 1:
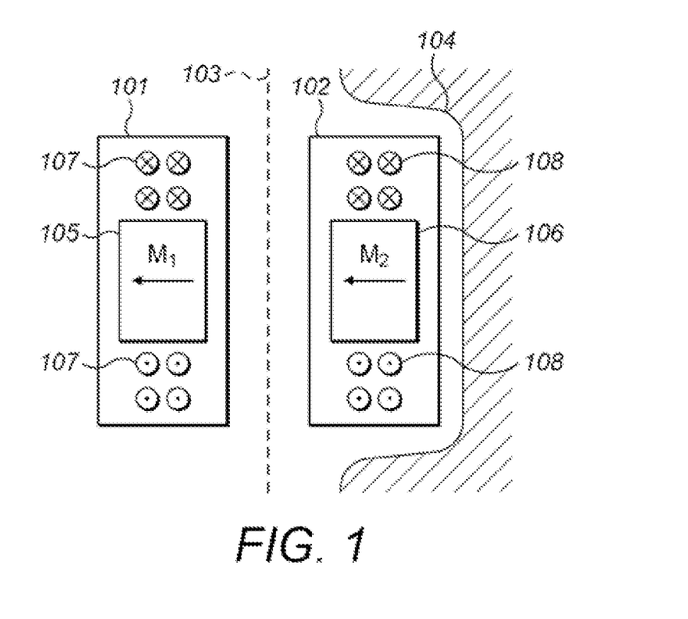
FIG. 1 shows a portion of a typical idealized cochlear implant which may be used in embodiments of the present invention.

Some implants such as for example Vestibular Implants, (VI's), Middle Ear Implants (MEI's) and Cochlear Implants (CI's) employ attachment magnets in the implantable part and an external part to hold the external part magnetically in place over the implant. For example, as shown in FIG. 1, a typical cochlear implant system may include an external transmitter housing 101 containing transmitting coils 107 and an external attachment magnet 105. The external attachment magnet 105 has a conventional coin-shape and a north-south magnetic dipole that is perpendicular to the skin of the patient to produce external magnetic field lines $M_1$ as shown. Implanted under the patient's skin is a corresponding receiver assembly 102 having similar receiving coils 108 and an internal attachment magnet 106. The internal attachment magnet 106 also has a coin-shape and a north-south magnetic dipole that is perpendicular to the skin of the patient to produce internal magnetic field lines $M_2$ as shown. The internal receiver housing 102 is surgically implanted and fixed in place within the patient's body. The external transmitter housing 101 is placed in proper position over the skin covering the internal receiver assembly 102 and held in place by interaction between the internal magnetic field lines $M_2$ and the external magnetic field lines $M_1$. Rf signals from the transmitter coils 107 couple data and/or power to the receiving coil 108 which is in communication with an implanted processor module (not shown).

Figure 2:
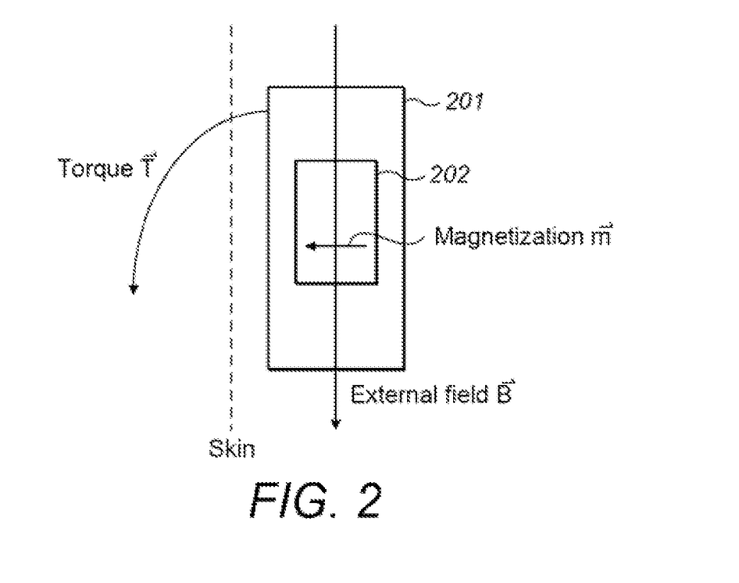
FIG. 2 shows effects of an external magnetic field on an implanted portion of an implanted part which may be used in embodiments of the present invention.

One problem arises when the patient undergoes Magnetic Resonance Imaging (MRI) examination. Interactions occur between the implant magnet and the applied external magnetic field $\vec{B}$ of the MRI. As shown in FIG. 2, the direction of the magnetic dipole moment $\vec{m}$ of the implant attachment magnet 202 is perpendicular to the skin of the patient. Thus, the external magnetic field $\vec{B}$ from the MRI may create a torque $\vec{\tau} = \vec{m} \times \vec{B}$ on the attachment magnet 202, which may displace the attachment magnet 202 or the whole implant housing 201 out of proper position. Among other things, this may damage the adjacent tissue in the patient. In addition, the external magnetic field $\vec{B}$ from the MRI may reduce, remove or invert the magnetic dipole moment $\vec{m}$ of the attachment magnet 202 so that it may no longer be strong enough to hold the external transmitter housing in proper position. The attachment magnet 202 may also cause imaging artifacts in the MRI image, as well as there are may be induced voltages in the receiving coil creating hearing artifacts. This is especially an issue with MRI field strengths exceeding 1.5 Tesla.

Thus, for existing implant systems with magnet arrangements, it is common to either not permit MRI, or at most limit use of MRI to lower field strengths. Other existing solutions include use of surgically removable attachment magnets, spherical attachment magnets (e.g. U.S. Pat. No. 7,566,296), and various ring magnet designs (e.g., U.S. Pat. No. 8,634,909 and U.S. Patent Publication 2011/0022120), all of which are incorporated herein by reference. Various other complex arrangements of magnetic elements have been described for use in hearing implant applications; See for example, U.S. Pat. Nos. 4,549,532 and 7,608,035, which are incorporated herein by reference. However, there is no suggestion that such therapeutic arrangements might potentially have any utility for magnetic attachment applications such as those described above.

SUMMARY OF THE INVENTION

Figure 3:
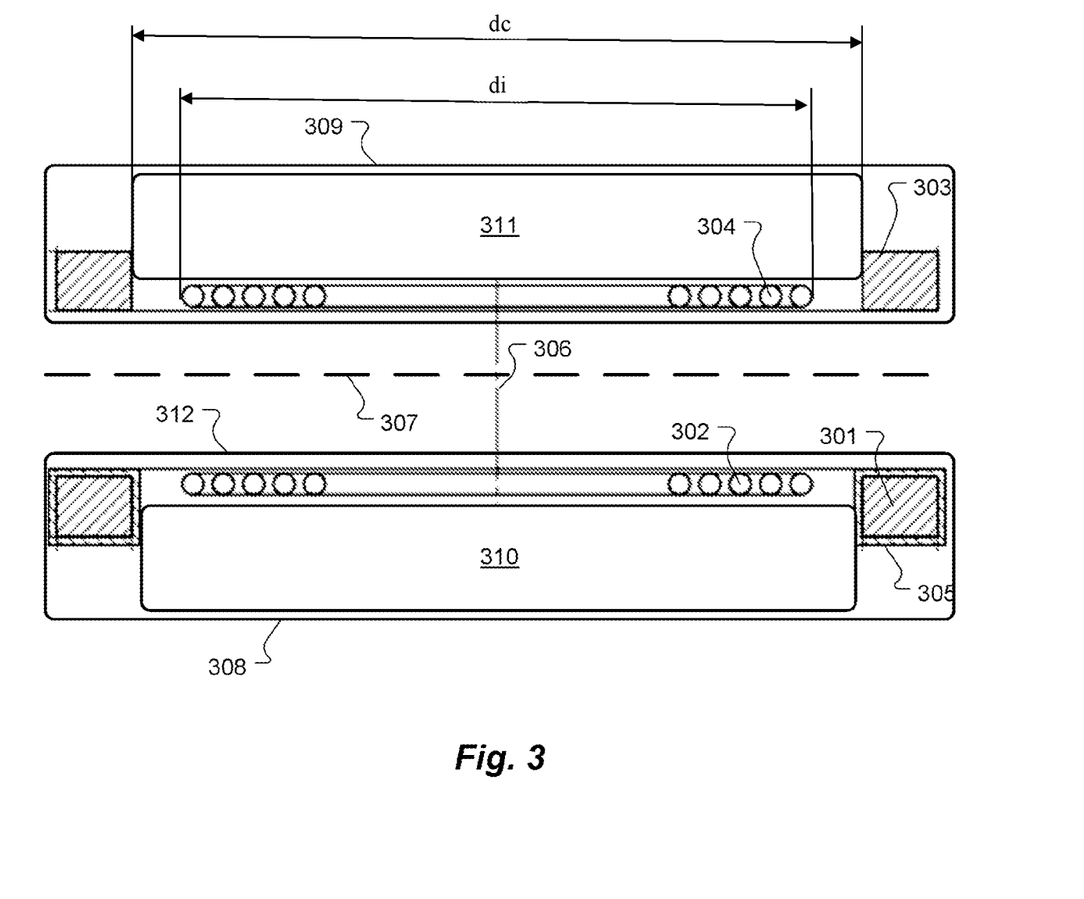
FIG. 3 shows a cross-sectional view of a coil and attachment magnet arrangement according to an embodiment of the present invention.

Embodiments of the present invention are directed to a magnetic system for a medical implant system. As shown in FIG. 3 planar implant receiver coil 302 is configured to lie underneath and parallel to overlying skin 307 of an implanted patient for transcutaneous communication of an implant communications signal. A planar ring-shaped attachment magnet 301 is also configured to lie underneath and parallel to the overlying skin 307 and radially surrounds the receiver coil. The attachment magnet 307 is characterized by local magnetic dipole moments configured to avoid creating or at least minimize torque on the attachment magnet in the presence of an external magnetic field. This can be achieved by a ratable diametrical overall magnetization or a complex magnetization where the integral of all local magnetic dipole moments is zero.

In further specific embodiments, there is an implant housing configured to contain the implant receiver coil and the attachment magnet. The implant housing and the attachment magnet may be configured to enable rotation of the attachment magnet within the implant housing to avoid creating torque on the attachment magnet in the presence of an external magnetic field. Or the implant housing and the attachment magnet may be configured to prevent rotation of the attachment magnet within the implant housing. There may be a volume of damping oil within the implant housing around the attachment magnet configured to resist movement of the implant magnet within the implant housing The attachment magnet may include multiple local magnetic sections, wherein each domain can be either radially or diametrically magnetized to enable a ring-magnet acting by connecting the single domains. The segmented magnet may have the same magnetic and MRI behavior as the described ideal ring magnet and may be encapsulate in a biocompatible material to guarantee mechanical and biological safety.

The attachment magnet may include multiple local magnetic sections, wherein each local magnetic field has an independent local magnetic field and an independent local magnetic field direction, and wherein a combined magnetic field for all the local magnetic fields has a zero overall magnetic dipole moment. In such an embodiment, each local magnetic section may be a physically distinct ring segment, whereby the attachment magnet comprises multiple ring segments connected together to form a ring shape. Or the attachment magnet may comprise a single integral structure without distinct ring segments. In another embodiment, the attachment magnet may be characterized by a single magnetic dipole moment oriented across the ring diameter parallel to the overlying skin.

The receiver coil may have a disk shape. And the attachment magnet is encapsulated in biocompatible material.

In any of the above, the medical implant system may be a hearing implant system such as a cochlear implant system, a middle ear implant system, a bone conduction hearing implant system, or a vestibular implant system.

DETAILED DESCRIPTION OF SPECIFIC EMBODIMENTS

Various embodiments of the present invention are directed to an improved implant attachment magnet arrangement that reverses the conventional structure. Instead of a cylinder-shaped attachment magnet surrounded by a ring-shaped receiver coil, embodiments of the present invention have a center receiver coil surrounded by a ring-shaped attachment magnet with one overall or locally varying magnetic dipole moment orientations. One advantage of the invention is, that the ring shape of the attachment magnet distributes the attractive magnetic holding force exerted to the external attractive magnetic holding part to a larger area around the center coil, compared to the conventional design where the attractive magnetic holding force is exerted to the external part from the small center magnet to a small area around the coil center only. Another advantage is, that the receiver and transmitter coils for transcutaneous transmission may use the area up to the transmitter or receiver coil center, such that a better coupling can be achieved. This in turn can improve in case of power transfer the power transfer efficiency and in case of data transfer the signal-to-noise ratio of the data signal at the receiver coil. Another advantage of the ring-shaped attachment magnet is, that the volume and hence the holding force exerted to the external part can be increased in comparison to the conventional design. The ring-shaped attachment magnet also offers greater internal space for electronic components, which can lead to a size reduced implant and a correspondingly smaller external part size as well. The internal space may have one sidewall facing the bone or skin of the patient head that may be adapted to fit the outer shape of the bone or skin for the implantable and external part respectively. For example, the sidewall may have a concave shape. For the external part this may further improve the attractive magnetic holding force distribution and thereby additionally increase the retention abilities and patient comfort.

FIG. 3 shows a planar implant receiver coil 302 surrounded by the ring-shaped attachment magnet 301, configured to be implantable in a patient underneath and parallel to the overlying skin 307 for transcutaneous communication. The Communication signals are transmitted from a corresponding transmitter coil 304 in an external part 309 which is held in place on the skin 307 by magnetic attraction by the attachment magnet 301. The implant receiver coil 302 and the attachment magnet 301 have a radially symmetric shape about a common center axis 306. The outer diameter (dc) of the receiver coil 302 is smaller than the inner diameter (di) of the attachment magnet 301. In one preferred embodiment, the ratio of the inner diameter (di) of the attachment magnet 301 to outer diameter (dc) of the receiver coil 302 is in the range from 0.74 to 0.76. The attachment magnet 301 interacts with an external attachment magnet 303 with a matching magnetic field to create the attachment force that holds the external part 309 securely in place on the skin 307 with the transmitter coil 304 directly over the receiver coil 302 for optimal coupling of the communications signal (that is for example generated in an external signal processor 311 that also may be located in the external part 309 as shown, or it may be located separately). The attachment magnet 301 may have any suitable magnetic dipole moment described herein by way of reference to any of the exemplary figures.

The specific embodiment shown in FIG. 3 includes an implant housing 308 that has an outer surface 312 that is configured to lie under and parallel to the skin 307 and contains the implant receiver coil 302 and the attachment magnet 301. The implant attachment magnet 301 may be covered within a magnet housing 305 of a biocompatible material to guarantee biocompatibility and mechanical resistance. The implant housing 308 also contains implant circuitry 310 that processes the implant communications signal from the receiver coil 302 to extract a power component to power the implanted components, and/or a data component that is processed into one or more stimulation signals for implanted electrodes (not shown). In one embodiment when implanted, the skull facing sidewall may be adapted to fit the outer shape of the skull bone, e.g. being concave shaped. In other embodiments, though, there may not be such an implant housing 308; for example, the receiver coil 302 and the attachment magnet 301 may be encapsulated in resilient material with the implant circuitry 310 physically separate. The resilient material may be silicone.

Figure 4:
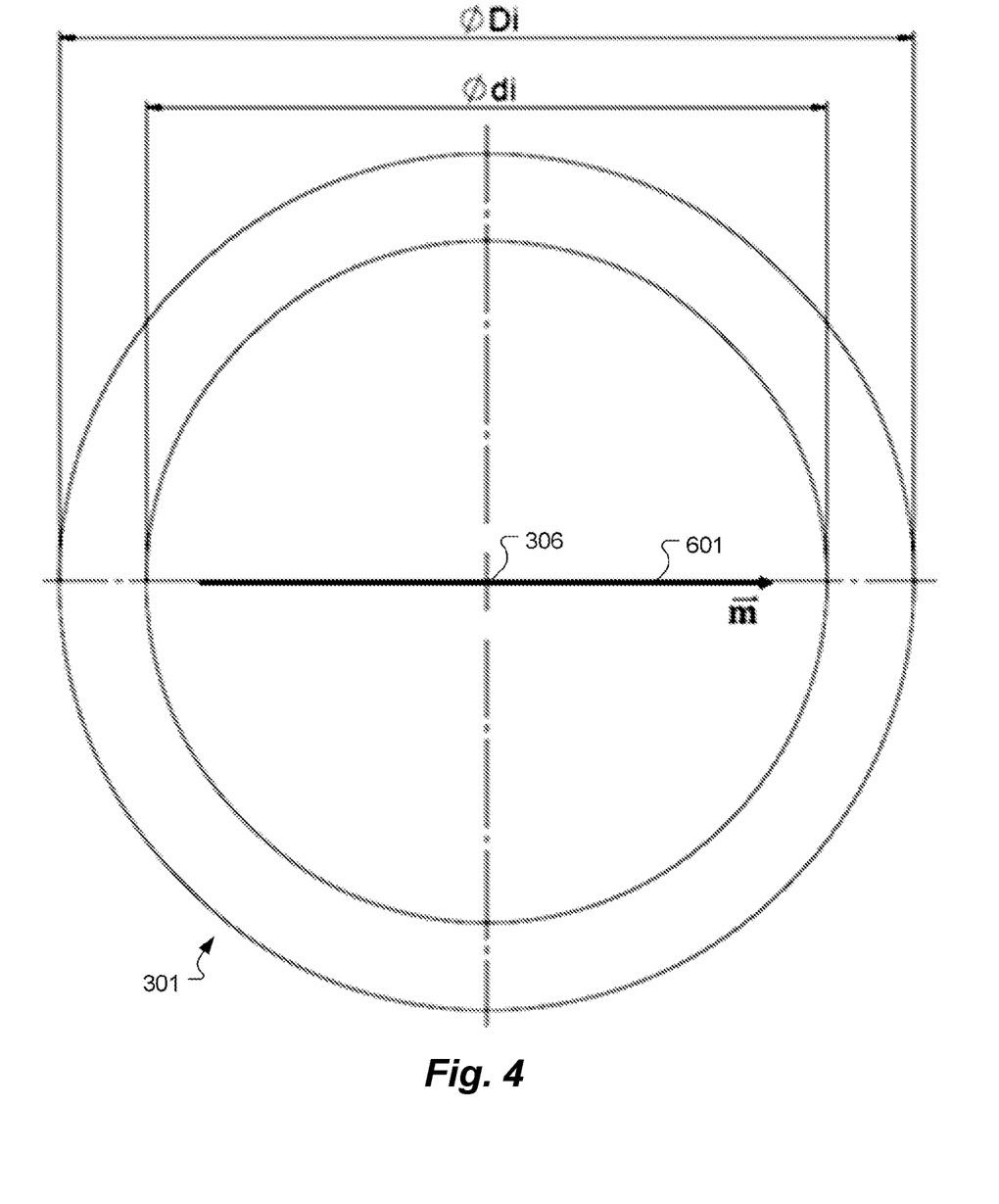
FIG. 4 shows a top plan view of an attachment magnet according to an embodiment of the present invention.

FIG. 4 shows a top plan view of another embodiment of an attachment magnet 301 according one aspect of the present invention, that is characterized by a single magnetic dipole moment 601 that is oriented across the ring diameter, i.e. diametrical magnetization, parallel to the overlying skin or parallel to the common center axis 306, i.e. axial magnetization, and perpendicular to the overlying skin (not shown) either oriented away or toward. An external applied magnetic field $\vec{B}$ from e.g. an MRI scanner may create a torque $\vec{B}$ on the attachment magnet 301. In one example, for improving MRI safety, the attachment magnet 301 may be fixated to the underlying bone by any suitable fixation means. This may for example be screws or pins as known in the art.

In another preferred embodiment, the attachment magnet 301 has a magnetic dipole moment 601 parallel to the skin and is rotatable around the common center axis 306 to align with the strong external magnetic field $\vec{B}$ from e.g. the MRI and thereby avoid creating a torque $\vec{B}$ about the common center axis 306 of the attachment magnet 301. This avoids, when implanted, contact force onto the skull and thus pain to the patient and may even prevent displacement of the attachment magnet 301 and thereby improves MRI safety. For this purpose, one or more sliding surfaces of the attachment magnet 301 may be covered by titanium or some other material to reduce frictional abrasion. In some embodiments, the attachment magnet 301 may be rotatable located in the interior volume of the magnet housing 305. At least one part of the interior volume of the magnet housing 305 may include a volume of damping oil or ferromagnetic domain(s) around the attachment magnet 301 in a configuration that resists unintended movements of the attachment magnet 301 within the magnet housing 305 due to for example movement of the patient head. The magnet housing 305 may be an integral part of implant housing 308, where the internal volume of the magnet housing 305 may be formed by a closed compartment in the implant housing 308. For this embodiment with a rotatable magnet design the magnet material must not resist high demagnetization fields inside of a strong external magnetic field, because the internal magnetic dipole moment is aligned to the external field resulting in no magnet material harm.

Figure 5:
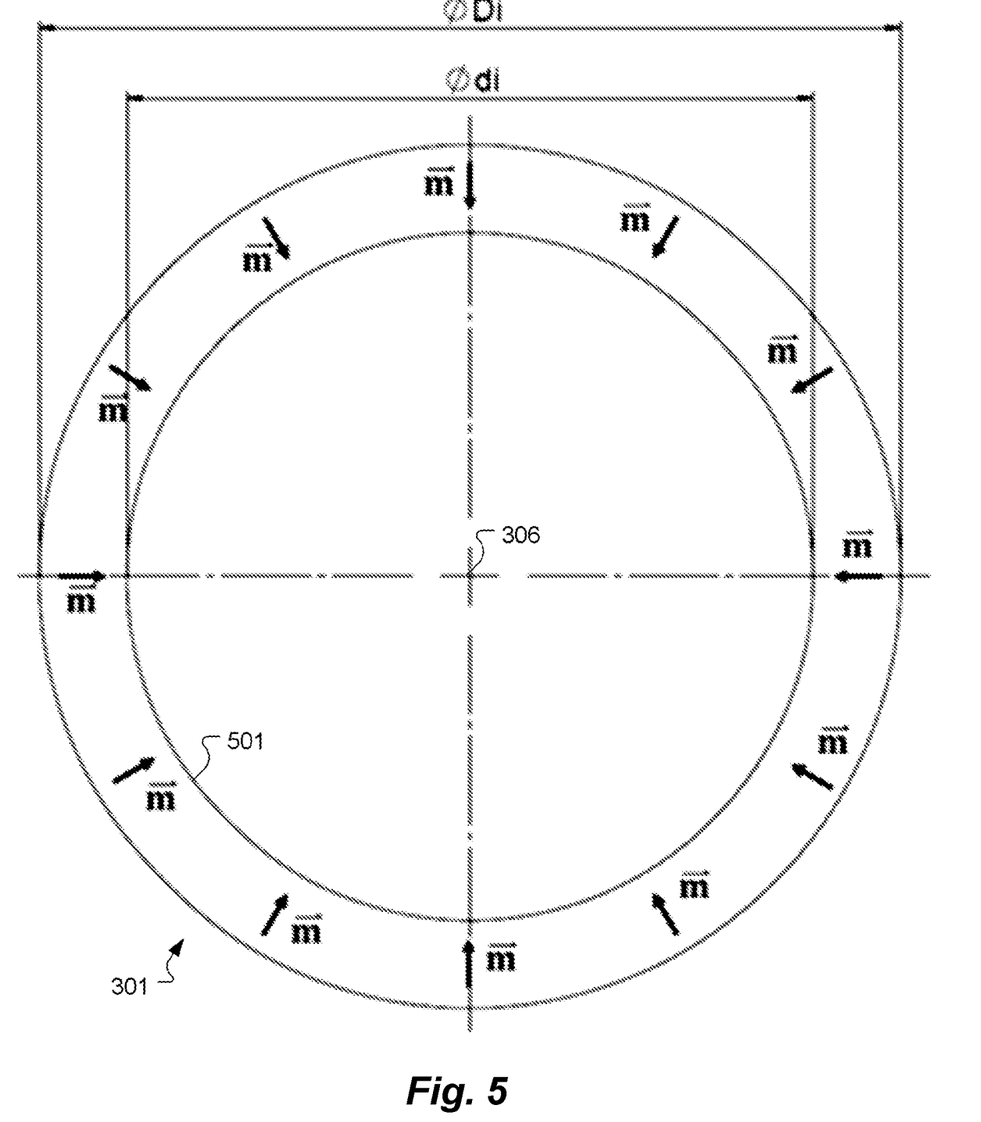
FIG. 5 shows a top plan view of an attachment magnet according to another embodiment of the present invention.

FIG. 5 shows a top plan view of an attachment magnet 301 with radial magnetization of the planar ring-shaped magnet design, where the magnetic dipole moment orientation $\vec{m}$ at each point is directed to the rotation symmetry axis 306. The corresponding attachment magnet 301 of the external part 309 has a magnetic dipole moment orientation $\vec{m}$ in the opposite direction to develop an attractive force, i.e. the magnetic dipole moment $\vec{m}$ at each point is directed away from the rotation symmetry axis of the external attachment magnet 301. This radial symmetric magnetization results in a net zero magnet dipole moment $\vec{m}$ and as a consequence no torque $\vec{T}$ on the attachment magnet 301 occurs when exposed to an external magnetic field $\vec{B}$, for example from a MRI scanner. In this embodiment, the magnet material used for the attachment magnet 301 must have the resistance against demagnetization, because at least one magnet domain is orientated opposite to the external magnetic field, for example from a MRI scanner.

Figure 6:
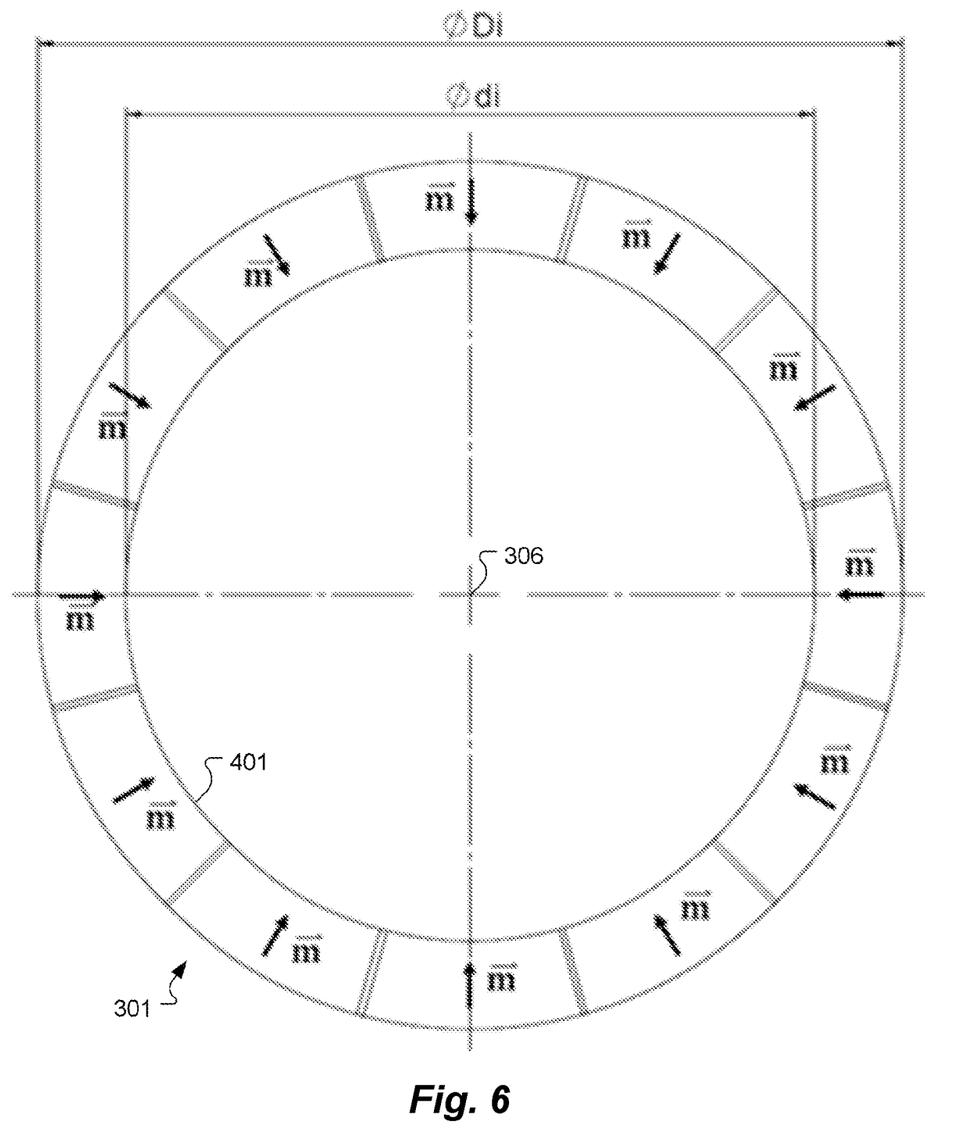
FIG. 6 shows a top plan view of an attachment magnet according to another embodiment of the present invention.

FIG. 6 shows a top plan view of an attachment magnet 301 showing an embodiment in which each local magnetic section is a physically distinct ring segment 401 whereby the attachment magnet 301 comprises multiple ring segments 401 connected together to form a ring shape. In this embodiment, each segment can either have a radial symmetric magnetic dipole moment $\vec{m}$ or a diametrical magnetic dipole $\vec{m}$ or a combination of both. As in FIG. 5, the symmetric magnetic arrangement results in a net zero magnetic dipole moment $\vec{m}$ and as a consequence no torque $\vec{T}$ on the attachment magnet 301 occurs when exposed to an external magnetic field $\vec{B}$. In this embodiment, the magnet material has to have the resistance against demagnetization, because at least one magnet segment 401 has a magnetic dipole moment $\vec{m}$ orientated into opposite direction to the external magnetic field $\vec{B}$, for example from a MRI scanner.

Figure 7:
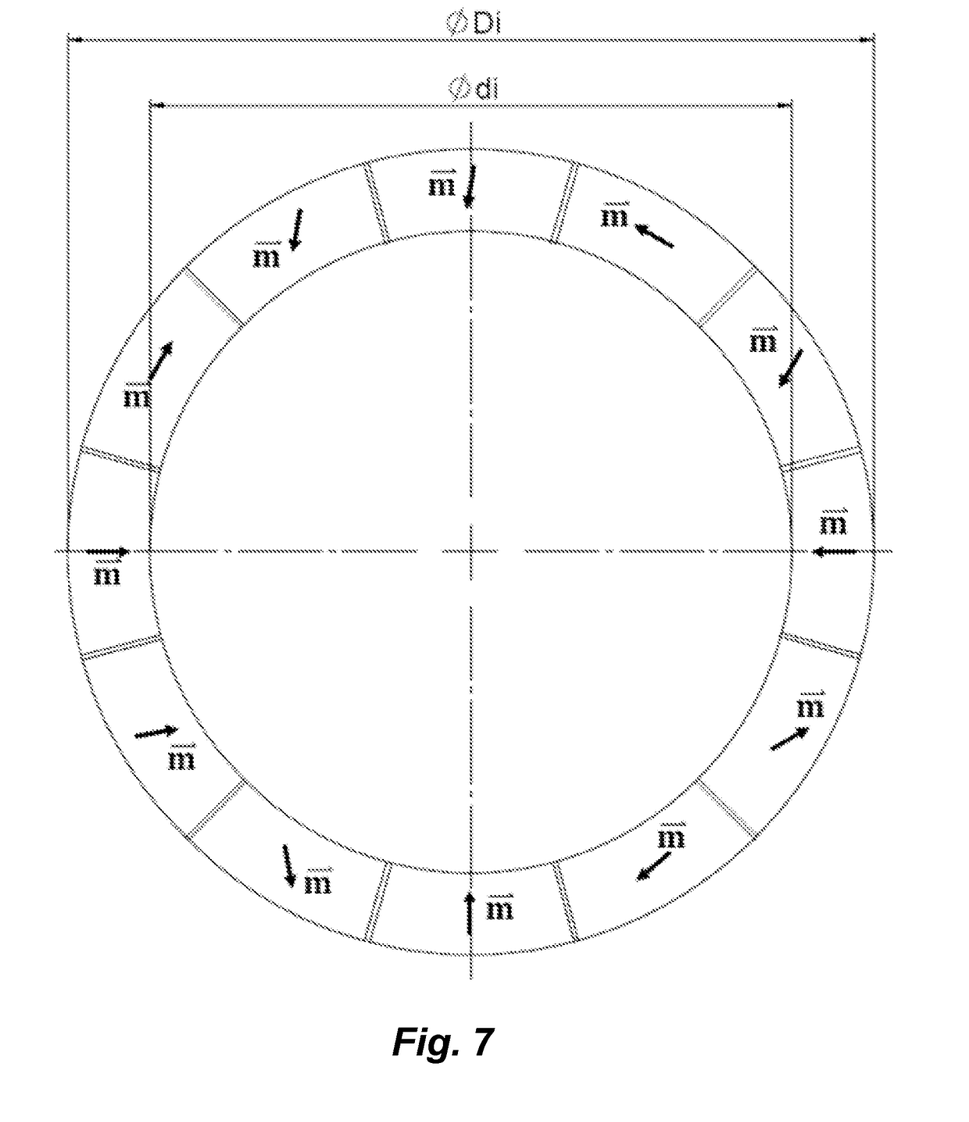
FIG. 7 shows a top plan view of an attachment magnet according to another embodiment of the present invention.

FIG. 7 shows a top plan view of an attachment magnet 301 showing an embodiment in which there are multiple local magnetic sections with each having an independent local magnetic dipole moment $\vec{m}$ and an independent local magnetic dipole moment orientation (as shown by the adjacent arrows) that in this example is parallel to the plane of the overlying skin. In one embodiment, the local magnetic sections and their local magnetic dipole moment $\vec{m}$ may be arranged and orientated in such a way, that the exerted holding force on the external attachment magnet 303 has at least one distinguished maximum at one rotational angle about the common center axis 306 relative to the attachment magnet 301. Such an exemplary arrangement is shown in FIG. 7. This has the advantage, that the external part 309 is held in place on the skin 307 in a fixed relative rotational relation to the (implanted) implant housing 308. This is for example important for Vestibular Implants where the movement sensors in the external part must have a known orientation in relation to the patient. In addition, the overall combined magnetic dipole moment for all the local magnetic dipole moments $\vec{m}$ together may have a zero combined magnetic dipole moment (the vector sum of the local magnetic dipole moments $\vec{m}$ as shown in FIG. 7 vanishes, i.e. for each section i having local magnetic dipole moment $\vec{m}$, the vector sum yields:

$$\sum_i \vec{m}_i = 0)$$

and as a consequence no torque $\vec{T}$ on the attachment magnet 301 occurs when exposed to an external magnetic field $\vec{B}$, for example from a MRI scanner.

Figure 8A:
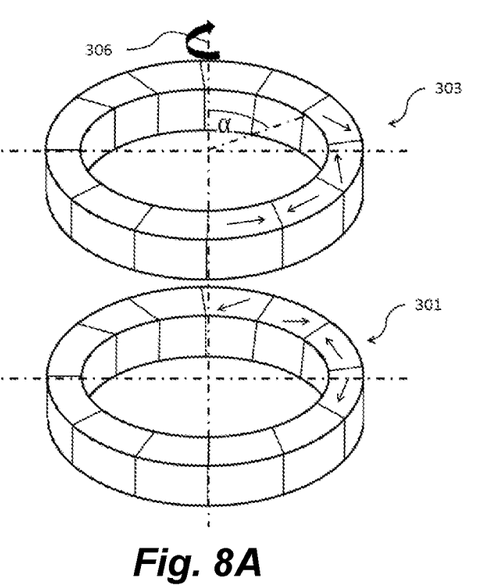
FIGS. 8A and 8B show an attachment magnet according to another embodiment in relation to an external attachment magnet and the holding force therebetween as a function of the rotational angle, respectively.
Figure 8B:
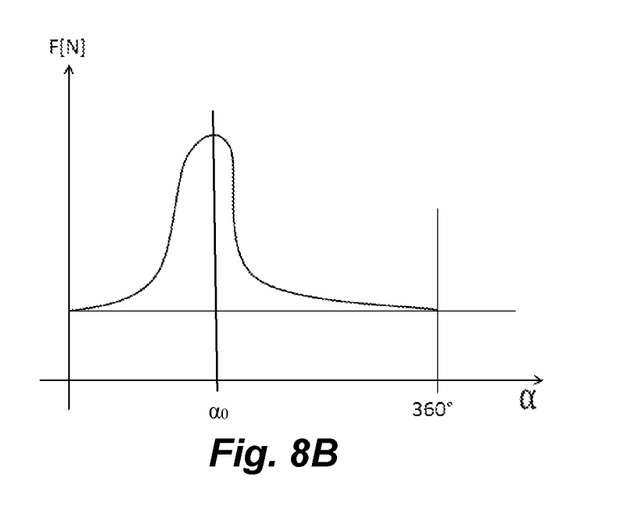

The attachment magnet 301 shown in FIG. 7 illustrates an example where the local magnetic sections and their local magnetic dipole moment are arranged in such a way, that the combined magnetic dipole moment vanishes and simultaneously the exerted holding force on a corresponding external attachment magnet 303 has at least one distinguished maximum at one rotational angle about the common center axis 306 relative to the attachment magnet 301. FIG. 8A shows the attachment magnet 301 in a configuration as shown in FIG. 7 and corresponding external attachment magnet 303 rotated relative to each other by angle α. The exemplarily shown four local magnetic segments 401 of the external attachment magnet 303 have opposite magnetic orientation in relation to their counterpart local magnetic segment 401 of the attachment magnet 301 to obtain maximal attractive force. FIG. 8B shows the attractive force between attachment magnet 301 and external attachment magnet 303 as a function of the rotational angle α about the common center axis 306. The force is strongest at one angle $\alpha_0$. In one embodiment, the attachment magnet 301 may be fixated, in the same way as described with reference to FIGS. 5 and 6 above. Similarly, the magnet material must be resistant against demagnetization, because at least one magnet sections has a magnetic dipole moment $\vec{m}$ orientated into opposite direction to the external magnetic field $\vec{B}$, for example from a MRI scanner.

In another embodiment, the attachment magnet 301 shown in FIGS. 7 and 8 may be rotatable about the common center axis 306 in relation to the implant housing 308, as shown in FIG. 4. In this configuration, the implantable part may comprise a sensor for detecting the relative rotational angle of the attachment magnet 301 in relation to the implant housing 308. The sensor may comprise a magnetic field sensor to measure the magnetic field of the attachment magnet 301 and provide to the implant circuitry 310. Implant circuit 310 may be configured to calculate the relative rotational angle in relation to implant housing 308 from the measurement. Alternatively, instead of the sensor, a spring element may be used to bring the attachment magnet 301 reversibly back to a pre-determined rotational angle in relation to the implant housing 308.

Although various exemplary embodiments of the invention have been disclosed, it should be apparent to those skilled in the art that various changes and modifications can be made which will achieve some of the advantages of the invention without departing from the true scope of the invention. For example, the ring-shape although shown as a circular ring, may have any suitable geometric form, for example and without limitation a rectangular, quadratic, triangular, oval with or without rounded edges.

What is claimed is:

1. A magnetic system for a hearing implant system for a patient user, the system comprising:
   an implant housing having:
   a ring-shaped implant receiver coil configured to lie underneath and parallel to overlying skin of an implanted patient for transcutaneous communication of an implant communications signal; and
   a ring-shaped attachment magnet configured to lie underneath and parallel to the overlying skin and radially surrounding the receiver coil,
   wherein the implant housing and the attachment magnet are configured to enable rotation of the attachment magnet within the implant housing in the presence of an external magnetic field, and
   wherein the implant housing further comprising a sensor adapted for determining the relative angle of rotation between the implant housing and the attachment magnet.

2. The system according to claim 1, wherein the implant receiver coil is planar.

3. The system according to claim 1, wherein the ring-shaped attachment magnet is planar.

4. The system according to claim 1, wherein the attachment magnet and receiver coil are circular or oval ring-shaped.

5. The system according to claim 4, wherein the ratio of the inner diameter of the ring-shaped attachment magnet to the outer diameter of the ring-shaped receiver coil is in the range from 0.74 to 0.76.

6. The system according to claim 1, wherein the attachment magnet is characterized by a single magnetic dipole moment.

7. The system according to claim 6, wherein the dipole moment is oriented across the ring diameter parallel to the overlying skin or parallel to the center axis of the ring-shaped attachment magnet and perpendicular to the overlying skin.

8. The system according to claim 1, wherein the attachment magnet comprises a plurality of local magnetic sections, wherein each of the local magnetic section has an independent local magnetic dipole and an independent local magnetic dipole orientation.

9. The system according to claim 8, wherein the combined magnetic dipole for all the local magnetic sections has a zero overall magnetic dipole moment.

10. The system according to claim 8, wherein the independent local magnetic dipoles are oriented such, that the exerted attractive holding force to an external part comprising a ring-shaped external attachment magnet where the attachment magnet and the external attachment magnet are aligned about a common center axis, has at least one distinguished maximum at one rotational angle about the common center axis relative to the attachment magnet.

11. The system according to claim 8, wherein each of the local magnetic sections is a physically distinct ring segment, wherein the attachment magnet comprises the plurality of the ring segments connected together to form the ring-shape.

* * * * *